[19] United States Patent
Koster et al.

[11] Patent Number: 4,978,811
[45] Date of Patent: Dec. 18, 1990

[54] PROCESS FOR HYDROLYSIS OF ORTHO-AROMATIC DI-ARYL ETHERS

[75] Inventors: Robert A. Koster; Philip J. Brondsema; Willis J. Pennington; William C. Sumner, all of Midland, Mich.; Susan E. Vilmer, Grapevine, Tex.

[73] Assignee: The Dow Chemical Company, Midland, Mich.

[21] Appl. No.: 176,533

[22] Filed: Apr. 1, 1988

[51] Int. Cl.$^5$ .................. C07C 37/50; C07C 39/00
[52] U.S. Cl. .................... 568/734; 568/731; 568/743; 568/744
[58] Field of Search ............. 568/731, 734, 743, 744

[56] References Cited

U.S. PATENT DOCUMENTS

| 1,914,557 | 6/1933 | Craver | 502/10 |
| 1,914,558 | 6/1933 | Craver | 502/10 |
| 2,095,619 | 10/1937 | Stoesser et al. | 252/462 |
| 3,363,002 | 1/1968 | Craggs | 568/630 |
| 3,522,275 | 7/1970 | Factor | 568/744 |
| 4,000,203 | 12/1976 | Gross et al. | 568/744 |
| 4,008,254 | 2/1977 | Gross et al. | 568/698 |
| 4,009,185 | 2/1977 | Fishel | 568/698 |
| 4,013,694 | 3/1977 | Fishel | 568/698 |
| 4,035,428 | 7/1977 | Fishel et al. | 568/744 |
| 4,156,698 | 5/1979 | Dwyer et al. | 585/408 |
| 4,258,218 | 3/1981 | Dwyer et al. | 568/698 |
| 4,278,816 | 7/1981 | Shim | 568/744 |
| 4,331,565 | 5/1982 | Schaefer et al. | 252/462 |
| 4,407,735 | 10/1983 | Sawamura | 502/10 |
| 4,473,713 | 9/1984 | Ratton | 568/744 |
| 4,638,098 | 1/1987 | Mossman | 568/630 |

FOREIGN PATENT DOCUMENTS

| 1062730 | 9/1979 | Canada | 568/809 |
| 911246 | 11/1962 | United Kingdom | 568/744 |
| 919088 | 2/1963 | United Kingdom | 568/743 |
| 959605 | 6/1964 | United Kingdom | 568/743 |
| 1236389 | 6/1971 | United Kingdom | 568/630 |

OTHER PUBLICATIONS

Whitesides et al., "Copper(I) Alkoxides. Synthesis, Reactions, and Thermal Decomposition," *J. of the Amer. Chem. Soc.*, 96:9, May 1, 1974, pp. 2829–2835.
*Encyclopedia of Chemical Technology*, 3rd Edition, vol. 9, pp. 384–385.
*Advanced Organic Chemistry*, "Reactions, Mechanisms, and Structure," 3rd Edition, 589 (1985).
Sabatier et al., *Academie Des Sciences*, "Preparation catalytique des oxydes phenoliques et des oxydes diphenyleniques," pp. 492–494.
Fishel et al., "O-Phenylphenol from Phenol: A Two-Step Selective Substitution Process," *Catalysis in Organic Synthesis*, pp. 119–132 (1980).

Primary Examiner—Werren B. Lone

[57] ABSTRACT

Ortho-aromatic diaryl ethers, such as o-biphenylyl phenyl ether, are hydrolyzed to corresponding phenolic compounds, such as o-phenylphenol and phenol, when contacted with water in the presence of ceria or thoria at a temperature of between about 250° C. and 700° C.

21 Claims, No Drawings

PROCESS FOR HYDROLYSIS OF ORTHO-AROMATIC DI-ARYL ETHERS

BACKGROUND OF THE INVENTION

The instant invention relates to the hydrolysis diaryl ethers to form phenolic compounds.

Diaryl ethers are ethers wherein an oxygen atom joins two aryl moieties. Hydrolysis of diaryl ethers yields phenolic compounds which correspond to the two aryl moieties. A current method of hydrolyzing diaryl ethers is by caustic hydrolysis. That method involves contacting the diaryl ether with water in a caustic aqueous solution at 425° C. and 5200 psig. The equipment to practice that process is extremely expensive because of the harsh reaction conditions necessary to effect hydrolysis.

Both ceria ($CeO_2$) and thoria ($ThO_2$) are known to catalyze the equilibrium hydrolysis and dehydration of diphenyl oxide and water to phenol and vice versa. Moss, *Improvements in and Relating to Hydration and Dehydration processes and to Catalysts therefor*, British Patent No. 911,246 (published Nov. 21, 1962)(dealing with thoria) and Fishel et al., "O-Phenylphenol from Phenol: A Two Step Selective Substitution Process," *Catalysis in Organic Synthesis* 119, 120 (W. Jones ed. 1980) (dealing with ceria). It is further known that ortho-cresol can be dehydrated in the presence of thoria to yield bis-(2-methylphenyl) ether. Sabatier et al., "Préparation Catalytique des Oxydes Phénoliques et des Oxydes Diphényléniques," 151 *Compt. Rend.* 492, 493 (1910). However, thoria catalysts are reported to be ineffective for dehydrating phenolic compounds with ortho substituents larger than methyl groups, such as secondary or tertiary alkyl groups. Clark, *Synthesis of Ethers*, British Patent No. 1,236,389 (June 23, 1971).

What is needed is an improved process for hydrolyzing diaryl ethers having ortho-aromatic substituents to form the corresponding phenolic compounds.

SUMMARY OF THE INVENTION

It has now surprisingly been discovered that ceria and thoria will catalyze the hydrolysis of diaryl ethers which contain aromatic substituents ortho to the ether oxygen. The present invention is a process for preparing ortho-aromatic phenolic compounds comprising contacting a diaryl ether, which contains at least one aromatic substituent ortho to the ether oxygen, with water in the presence of a catalytic amount of catalyst comprising ceria, thoria or a combination thereof at a temperature and pressure sufficient to form phenolic compounds.

Ortho-aromatic phenolic compounds produced by the process of the present invention are useful as reagents, as intermediates for making dyes and synthetic rubbers, as preservatives and as biocides.

DETAILED DESCRIPTION OF THE INVENTION

Ethers which are hydrolyzed in the present process comprise two aryl groups joined by an oxygen atom. The aryl groups may be heterocyclic, but are preferably carbocyclic and more preferably hydrocarbyl. The aryl groups preferably comprise no more than about 10 carbon atoms; more preferably, no more than about 6 carbon atoms.

An aromatic substituent must be located on at least one aryl group ortho to the ether oxygen. (For the sake of clarity, aryl groups bonded directly to the ether oxygen shall be referred to as aryl groups, and aromatic groups which are an ortho substituent on an aryl group shall be referred to as aromatic substituents.) Aromatic substituents located ortho to the ether oxygen may be heterocyclic but are preferably carbocyclic and more preferably hydrocarbyl. Each substituent preferably comprises no more than about 10 carbon atoms; more preferably, no more than about 6 carbon atoms.

The aromatic substituent may be either fused or unfused with the aryl group. If fused, then the aromatic substituent and aryl group together form a polycyclic system with the ether oxygen bonded adjacent to a ring junction carbon; for instance, a 1-naphthyl, a 1- or 9-anthracyl or a 1-, 4- or 9-phenanthryl group. If unfused, then the aromatic substituent and aryl group together form a group such as a biphenylyl group. The most preferred aryl groups with aromatic substituents are the o-biphenylyl group, the 1-naphthyl group and homologs thereof.

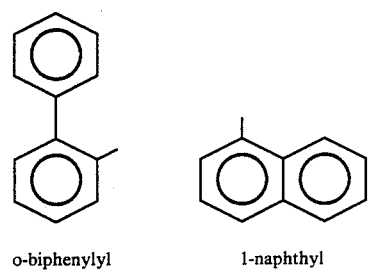

o-biphenylyl     1-naphthyl

Preferably, only one aryl group in each ether molecule has an ortho substituent. Examples of highly preferred ethers with aromatic substituents include o-biphenylyl phenyl ether and 1-phenoxynaphthalene.

Ethers used in the present invention can be formed by known methods for the preparation of diaryl ethers. For instance, they may be formed by the reaction of an ortho-aromatic aryl halide, such as o-bromophenylbenzene or 1-iodonaphthalene, with a phenolic compound or phenoxide salt in the presence of a catalyst such as copper or copper salt. Such condensations of aromatic compounds are well-known in the art and are described in March, *Advanced Organic Chemistry* 589 (3rd Ed. 1985); 9 *Kirk-Othmer Encyclopedia of Chemical Technology, Ethers,* 384–85 (3rd Ed. 1980); and Whitesides et al., "Copper(I) Alkoxides. Synthesis, Reactions, and Thermal Decomposition", 96 *J. Am. Chem Soc.* 2829, 2835 (1974), all of which are incorporated herein by reference. Ortho-aromatic ethers can also be synthesized by the processes described in Stoesser, *Aryl Oxides*, U.S. Pat. No. 2,095,619 (Oct. 12, 1937); McCall et al., *Process for the Arylation of Aromatic Compounds*, British Patent No. 919,088 (publ. Feb. 20, 1963); and Bain et al., *Process for the Arylation of Aromatic Compounds*, British Patent No. 959,605 (publ. June 3, 1964), all of which are incorporated herein by reference.

Certain ortho-aromatic diaryl ethers are commercially available. For instance, biphenylyl phenyl ether is commercially available in a mixture with diphenyl ether as DOWTHERM G* heat transfer medium. The o-biphenylyl phenyl ether can be isolated by known techniques such as distillation.

(*Trademark of The Dow Chemical Company.)

Water used in connection with the present process is preferably distilled water or piped steam free of catalyst poisons. The molar ratio of water to diaryl ether is preferably at least about 7:1 and more preferably at least about 25:1. The molar ratio of water to ether is preferably at most about 100:1; more preferably, at most about 70:1; and most preferably, at most about 50:1.

Catalysts useful in the present invention comprise cerium oxide, $CeO_2$, commonly known as ceria, thorium oxide, $ThO_2$, commonly known as thoria, or a combination thereof. Because thoria is a low level radiation hazard, the catalyst most conveniently comprises ceria without thoria.

The ceria and/or thoria may be used without a support, but is preferably dispersed on a support. Any conventional support, such as silica, alumina, titania or a zeolite, may be used. The support is preferably metal oxide and more preferably alumina. In experiments carried out by the inventors, a catalyst comprising ceria supported on γ-alumina had a lower initial conversion rate but a longer useful life than a catalyst comprising ceria supported on α-alumina. The weight of ceria on the support is preferably about 10 to 20 percent of the weight of the ceria and support together; more preferably, about 15 percent. The weight of thoria on the support is preferably about 10 to 35 percent of the weight of the thoria and support together; more preferably, about 20 to 30 percent.

The catalyst should have a surface area sufficient to expose an adequate amount of catalyst to the reagents so that substantial conversion of ether can occur. Although other known physical embodiments for catalysts may be used, preferred catalysts comprise particles of support material with ceria and/or thoria dispersed thereon. The diameters of the catalyst particles are preferably no larger than about 10 percent of the diameter of the reactor. More preferably, catalyst particles have a diameter of at least about 1/16 inch and at most about ⅛ inch. The surface area of the catalyst is preferably at least about $5 m^2/g$ and at most about $200 m^2/g$.

Catalysts useful in the practice of the instant invention are commercially available. They may also be prepared by the following process. First, alumina spheres are crushed and sieved to the desired particle size. Second, the alumina is dried. Third, an aqueous solution containing a nitrate of the desired catalyst metal, such as $Ce(NO_3)_3.6H_2O$, is added to the crushed alumina and permitted to dry. Fourth, the metal nitrate is oxidized in a furnace under air to metal oxide. Other known methods for depositing ceria on a support may also be used. Such methods are discussed in Sawamura, *Method of Impregnating Spheres of Activated Alumina for Use in Catalyst Support with Cerium*, U.S. Pat. No. 4,407,735 (Oct. 4, 1983) and Schaefer et al., *Method for Forming High Surface Area Catalyst Carrier and Catalyst Using Same*, U.S. Pat. No. 4,331,565 (May 25, 1982), which are incorporated herein by reference.

In the process of the present invention, the diaryl ether is contacted with the water in the presence of the catalyst. The temperature of the reaction is any temperature at which product forms and products do not undergo substantial side reaction while in the reactor. The minimum temperature for the reaction is preferably about 250° C., more preferably about 450° C., and most preferably about 490° C. The maximum temperature for the reaction is preferably about 700° C., more preferably about 600° C. and most preferably about 560° C. Too high a temperature can cause carbonized deposits to build up upon the catalyst, reducing catalyst efficiency. Too low a temperature can slow the rate of hydrolysis and reduce the level of conversion from ether to phenolic compound. At higher temperatures, such as about 550° C. or more, the degradation of catalyst efficiency can be slowed by using a higher molar ratio of water to ether, for instance about 50:1 or more.

The present invention may be practiced at any pressure under which hydrolysis occurs. The pressure is preferably no more than about 5 atmospheres. In ordinary catalytic reactors a pressure of 1 to 2 atmospheres is necessary to drive the reagents through the reactor, and the present process is conveniently run at such pressures.

A preferred method to practice the present invention is to heat the reagents and flow them simultaneously through a heated reactor containing the supported catalyst. The flow rate is preferably no more than about 125 moles of ether per mole of ceria or thoria per hour, more preferably no more than about 10 moles of ether per mole of ceria or thoria per hour and most preferably no less than about 0.05 moles of ether per mole of ceria or thoria per hour.

The ratio of conversion from ether to phenolic product depends to a great extent on the catalyst chosen, the temperature of the reaction, the amount of water present and the ether being hydrolyzed. When o-biphenylyl phenyl ether is hydrolyzed under most preferred conditions with a catalyst comprising about 17 percent ceria by weight on γ-alumina, the initial conversion on a single pass through the reactor is at least about 10 to about 20 percent. The conversion for 1-phenoxynaphthalene under similar conditions may exceed about 50 percent. The initial conversion for o-biphenylyl phenyl ether under most preferred conditions using a catalyst of 25 percent thoria on α-alumina is preferably at least about 15 percent and more preferably at least about 30 percent.

When a single pass does not give adequate levels of conversion, the phenolic product may be separated by known techniques, such as distillation or extraction, and the unreacted ether and water may be recycled through the process until adequate levels of conversion are obtained. Continued use of the catalyst ordinarily causes some deactivation. The catalyst can be regenerated by known techniques, such as burning off carbonaceous deposits with oxygen.

The instant invention is particularly useful in that it permits the hydrolysis of o-biphenylyl phenyl ether to o-phenylphenol and phenol. Both products currently have extensive markets. Although a single pass through the catalyst does not give complete conversion, the o-biphenylyl phenyl ether may be separated from the products and recycled through the catalyst until it is essentially completely converted.

ILLUSTRATIVE EXAMPLES

The following examples are for illustrative purposes only and are not intended to limit the scope of either the specification or the claims. All parts and percentages given herein are by weight unless otherwise specified.

EXAMPLE 1

Hydrolysis of with a Ceria Catalyst

Alumina spheres (Norton SA 3232) are crushed and sieved to −4/+7 U.S. scale mesh. The spheres are dried at 150° C. in a vented oven until a 10-g sample of the crushed alumina will hold 7.5 g of water before runoff is observed.

A sample of 65 percent aqueous solution of Ce(NO₃)₃.6H₂O weighing 128.4 g and containing 0.19 mole of cerium is diluted with deionized water to 140 g. The dilute solution is added evenly to 187.5 g of the dried alumina in a shallow Pyrex dish. After drying overnight at room temperature, the catalyst is further dried at 150° C. and then oxidized for 2 hours in a quartz tube furnace at 550° C. under an air flow of one liter per minute. The material recovered is about 17 percent ceria by weight on alumina.

A one-inch diameter tubular reactor is packed with 12 inches of alumina, then about 116 g of the catalyst previously prepared, and then about 4 inches of alumina. The reactor is installed in a furnace and the catalyst is heated to about 500° C. while water is introduced into the reactor at a rate of 200 ml/hr. Once the reactor temperature is steady at 500° C., air is introduced at 400 cm³/min. over a one-hour period to make sure the catalyst is in a fully regenerated state. Thereafter, the temperature of the reactor is reduced to 490° C. and the water feed is reduced to 72 ml/hr.

A sample of 95 percent o-biphenylyl phenyl ether is added to the reactor at 33 ml/hr. The other 5 percent of the sample is a mixture which includes m- and p-biphenylyl phenyl ether and 1- and 2-phenoxynaphthalene. Organic effluent from the reactor is analyzed by gas chromatography. The effluent comprises by mole about 82.9 percent o-biphenylyl phenyl ether and 11.4 percent o-phenylphenol (about 16.6 percent conversion); and about 0.807 percent 1-phenoxynaphthalene and about 0.628 percent 1-naphthol (about 54.3 percent conversion).

EXAMPLE 2

Hydrolysis with a Thoria Catalyst

A 30-inch long, 1-inch outer diameter stainless steel reactor is packed with 17½α inches of alumina pellets, with about 8 inches (100 g) of 25 percent by weight thoria on α-alumina and with about 4½α inches of alumina pellets forming three separate zones with the thoria catalyst in the middle. The reactor is heated to 490° C. and flow of water is begun as described in Example 1. An organic feed comprising about 93.0 percent by weight o-biphenylyl phenyl ether is passed through the reactor at a rate of about 60 ml per hour. The flow of water and ether are such that the reactants preheat in the 17½ inches of alumina pellets before reaching the catalyst. Sufficient water passes through the reactor that the weight ratio of water to organic is about 2:1. The makeup of the effluent is measured by gas chromatography. After about 15 minutes, the conversion of o-biphenylyl phenyl ether to o-phenylphenol and phenol is at least about 20 percent.

What is claimed is:

1. A process for preparing ortho-aromatic phenolic compounds comprising contacting a diaryl ether, which contains at least one aromatic substituent ortho to the ether oxygen, with water in the presence of a catalytic amount of catalyst comprising ceria, thoria or a combination thereof at a temperature and pressure sufficient to form phenolic compounds.

2. The process of claim 1 wherein each aryl group in the diaryl ether is carbocyclic, and each aryl group and each aromatic substituent independently comprises no more than about 10 carbon atoms.

3. The process of claim 2 wherein the catalyst comprises ceria, thoria or a combination thereof distributed upon a support.

4. The process of claim 3 wherein the temperature of the process is between about 250° C. and about 700° C.

5. The process of claim 4 wherein the temperature of the process is between about 475° C. and about 560° C.

6. The process of claim 4 wherein the molar ratio of water to ether is between about 7:1 and about 100:1.

7. The process of claim 6 wherein the molar ratio of water to ether is between about 25:1 and about 70:1.

8. The process of claim 6 wherein each aryl group and aromatic substituent is hydrocarbyl.

9. The process of claim 8 wherein each aromatic substituent independently comprises no more than about 6 carbon atoms.

10. The process of claim 9 wherein each diaryl ether contains only one ortho-substituted aryl moiety.

11. The process of claim 10 wherein the diaryl ether is o-biphenylyl phenyl ether, 1-phenoxynaphthalene or a homolog thereof.

12. The process of claim 6 herein the support is silica, titania, alumina or a zeolite.

13. The process of claim 12 wherein the catalyst comprises between about 10 and about 20 percent ceria by weight on alumina.

14. The process of claim 12 wherein the catalyst comprises about 20 to about 30 percent by weight thoria on alumina.

15. The process of claim 6 wherein the level of conversion from ether to phenolic compound on a single pass through the catalyst is at least about 10 percent.

16. The process of claim 13 wherein the level of conversion on a single pass through the catalyst is at least about 10 percent.

17. The process of claim 2 wherein the temperature of the process is between about 250° C. and about 700° C. and the molar ratio of water to ether is between about 7:1 and about 100:1.

18. The process of claim 17 wherein each aromatic substituent independently comprises no more than about 6 carbon atoms.

19. The process of claim 18 wherein each diaryl ether contains only one ortho-substituted aryl moiety.

20. The process of claim 19 wherein the diaryl ether is o-biphenylyl phenyl ether, 1-phenoxynaphthalene or a homolog thereof.

21. The process of claim 19 wherein the temperature of the reaction is at least about 550° C. and the ratio of water to ether in the reaction is at least about 50:1.

* * * * *

UNITED STATES PATENT AND TRADEMARK OFFICE
CERTIFICATE OF CORRECTION

PATENT NO. : 4,978,811

DATED : December 18, 1990

INVENTOR(S) : Robert A. Koster, Philip J. Brondsema, Willis J. Pennington, William C. Sumner, and Susan E. Vilmer It is certified that error appears in the above-identified patent and that said Letters Patent is hereby corrected as shown below:

Column 5, line 38, " $17\frac{1}{2}a$ inches " should correctly read -- $17\frac{1}{2}$ inches --.

Column 5, line 40, " $4\frac{1}{2}a$ inches " should correctly read -- $4\frac{1}{2}$ inches --.

Signed and Sealed this

Ninth Day of February, 1993

Attest:

STEPHEN G. KUNIN

Attesting Officer      Acting Commissioner of Patents and Trademarks